(12) United States Patent
Buschnakowski et al.

(10) Patent No.: US 10,511,122 B2
(45) Date of Patent: Dec. 17, 2019

(54) SENSOR ARRANGEMENT FOR USE IN PROCESS AUTOMATION

(71) Applicant: Endress+Hauser Conducta GmbH+Co. KG, Gerlingen (DE)

(72) Inventors: Stephan Buschnakowski, Chemnitz (DE); Steffi Krönert, Limach-O (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 173 days.

(21) Appl. No.: 15/653,596

(22) Filed: Jul. 19, 2017

(65) Prior Publication Data
US 2018/0034204 A1   Feb. 1, 2018

(30) Foreign Application Priority Data
Jul. 26, 2016   (DE) .................. 10 2016 113 763

(51) Int. Cl.
*G01N 27/36* (2006.01)
*H01R 13/627* (2006.01)
(Continued)

(52) U.S. Cl.
CPC ......... *H01R 13/6277* (2013.01); *G01D 11/30* (2013.01); *G01N 27/333* (2013.01);
(Continued)

(58) Field of Classification Search
CPC ... H01R 13/6277; H01R 35/04; H01L 25/167; G01N 27/36; G01N 27/333; G01D 11/30
See application file for complete search history.

(56) References Cited

U.S. PATENT DOCUMENTS 3,995,209 A * 11/1976 Weston ............... H01F 38/14
323/355
6,476,520 B1 * 11/2002 Bohm ............... H01F 38/14
307/104
(Continued)

FOREIGN PATENT DOCUMENTS

CN    101208596 A   6/2008
CN    101556240 A   10/2009
(Continued)

OTHER PUBLICATIONS

Search Report for German Patent Application No. 10 2016 113 763.4, German Patent Office, dated Apr. 5, 2017, 10 pp.
(Continued)

*Primary Examiner* — David J Bolduc
(74) *Attorney, Agent, or Firm* — Christopher R. Powers; PatServe

(57) ABSTRACT

The present disclosure relates to a sensor arrangement for use in process automation, having a sensor, comprising a first coupling body, having at least one sensor element for detecting a measurement value of the process automation, and a first interface for transmitting a signal dependent upon the measurement value, a connection element for transmitting the signal to a superordinate unit, comprising a second coupling body complementary to the first coupling body, having a second interface complementary to the first interface, wherein the first and second interfaces are designed for bi-directional communication between sensor and superordinate unit, where the sensor has at least one light source for transducing the signal dependent upon the measurement value into light of a color corresponding to the measurement value.

11 Claims, 3 Drawing Sheets

(51) Int. Cl.
*G01D 11/30* (2006.01)
*G01N 27/333* (2006.01)
*H01L 25/16* (2006.01)
*H01R 35/04* (2006.01)

(52) U.S. Cl.
CPC .......... *G01N 27/36* (2013.01); *H01L 25/167* (2013.01); *H01R 35/04* (2013.01)

(56) References Cited

U.S. PATENT DOCUMENTS

| | | | | |
|---|---|---|---|---|
| 6,705,898 | B2* | 3/2004 | Pechstein | G01N 27/286 439/660 |
| 2002/0047576 | A1* | 4/2002 | Gurthrie | H05B 33/0821 315/169.3 |
| 2005/0194296 | A1* | 9/2005 | Lin | C02F 1/76 210/85 |
| 2006/0133073 | A1* | 6/2006 | Nakata | H01L 25/167 362/192 |
| 2007/0184704 | A1* | 8/2007 | Blaak | H01R 13/6633 439/354 |
| 2008/0053255 | A1* | 3/2008 | Furey | G01D 11/245 73/866.5 |
| 2008/0206547 | A1* | 8/2008 | Nishio | G01N 27/36 428/319.1 |
| 2009/0134043 | A1* | 5/2009 | Ward | G01N 27/4168 205/792 |
| 2010/0182022 | A1* | 7/2010 | Lee | G01N 27/36 324/693 |
| 2011/0186447 | A1* | 8/2011 | Boeck | G01N 21/8507 205/787.5 |
| 2011/0241030 | A1* | 10/2011 | Kim | H01L 25/16 257/88 |
| 2012/0091008 | A1* | 4/2012 | Muir | G01N 27/333 205/316 |
| 2014/0257139 | A1* | 9/2014 | Arkwright | G01L 1/246 600/587 |
| 2017/0309798 | A1* | 10/2017 | Bonar | H01L 27/156 |

FOREIGN PATENT DOCUMENTS

| | | | |
|---|---|---|---|
| CN | 104053991 A | 9/2014 | |
| DE | 102006005632 A1 | 8/2007 | |
| DE | 102010005355 A * | 7/2011 | ............ G01N 27/36 |
| WO | 2012085757 A2 | 6/2012 | |

OTHER PUBLICATIONS

Wikipedia, Diffusor (Optik), https://de.wikipedia.org/w/index.php?title+Diffusor_(Optik)&oldid=1, 2 pp. (last accessed Apr. 5, 2017).

* cited by examiner

SENSOR ARRANGEMENT FOR USE IN PROCESS AUTOMATION

CROSS-REFERENCE TO RELATED APPLICATION

The present application is related to and claims the priority benefit of German Patent Application No. 10 2016 113 763.4, filed on Jul. 26, 2016, the entire contents of which are incorporated herein by reference.

TECHNICAL FIELD

The present disclosure relates to a sensor arrangement for use in process automation, including a sensor and a connection element.

BACKGROUND

In process automation, sensors are connected to a connection element by means of a mechanical coupling, often by means of a bayonet joint. The connection element comprises a cable approach and a cable. The cable is in turn connected to a superordinate unit for instance, a measuring transducer or a control station. Respectively located at the sensor and connection element is an interface, for instance, of inductive or optical design via which the sensor is supplied with power and communication from the sensor to the connection element or to the superordinate unit is ensured.

The pH value plays a large role in the monitoring, control, and regulation of many chemical reactions. Therefore, it is often necessary to know an exact pH value. There is a plurality of different glass pH sensors which are available for the most varied applications. A determination of the respective pH value of a solution with a sensor is normally possible only by reading off a numerical value at a measuring transducer.

Among other things, these glass pH sensors may also be used in a laboratory setting. Measuring transducers are used in which up to 8 pH sensors may be connected. For the user to obtain even just an approximate impression of the measurement value, the user must read off the measurement value. Often, corresponding adjustments must also be made in the menu navigation.

With such pH sensors, it is disadvantageous that a quick determination of the pH value is not possible for the user.

SUMMARY

The present disclosure is based upon the aim of providing a pH sensor that allows a quicker determination of the pH value by the user.

The aim is achieved by the subject matter of the present disclosure. The subject matter of the present disclosure is a sensor arrangement for use in process automation, having a sensor, including a first coupling body, having at least one sensor element for detecting a measurement value of the process automation, and a first interface for transmitting a signal dependent upon the measurement value, a connection element for transmitting the signal to a superordinate unit, comprising a second coupling body complementary to the first coupling body, having a second interface complementary to the first interface, wherein the first and second interfaces are designed for bi-directional communication between sensor and superordinate unit, wherein the sensor has at least one light source for transducing the signal dependent upon the measurement value into light of a color corresponding to the measurement value.

A pH sensor that visualizes the broad spectrum of pH values from 0 to 14, analogous to the measurement range of universal test paper, optically via color change, thereby has many advantages. With exact adjustment of the pH value of a solution, the desired value is approached via addition of acidic or alkaline media. This approach can now be observed via an optical color progression at the sensor, and a very convenient addition of the respective chemicals is provided. Continuous verification through visual monitoring of the measurement device display is not necessary. However, when the desired pH value is approached, it is immediately possible to make the precise adjustment at the measuring transducer via the indicated measurement value of the pH sensor.

The pH value also changes during the course of many chemical reactions. With a pH sensor that visually represents the pH value via a light indicator, the progress of the reaction can also be observed from a certain distance. That means that the continuous monitoring via the measurement device is not necessary. Here as well, however, the precise measurement value can be determined via the calibrated sensor if needed, i.e., as soon as one approaches the desired reaction end.

The display of a broad pH spectrum via an optical realization, combined with precise measurement technology, results in an enormous relief in laboratory work.

According to one embodiment, the optical realization of the light source includes at least one red light-emitting diode, at least one green light-emitting diode, and at least one blue light-emitting diode.

According to an embodiment, the at least one light source is arranged at the second coupling body or at the sensor element.

According to a further embodiment, the sensor element comprises glass, wherein the at least one light source is arranged in such a way in the second coupling body that the emitted light is directed in the glass of the sensor element and is emitted from the glass.

According to a further embodiment, the at least one light source has a diffuser which is arranged in such a way that the emitted light is diffusely radiated.

According to at least one embodiment, the sensor has a microcontroller for directing the light-emitting means.

According to a further embodiment, measurement values that correspond to color transitions of pH indicators are stored in the microcontroller.

According to an embodiment, the corresponding color transitions can be chosen by a user.

According to a further embodiment, the measurement value is the pH value, wherein the color that corresponds to the measurement value is the color of a pH indicator for the determined pH value.

BRIEF DESCRIPTION OF THE DRAWINGS

The present disclosure is explained in more detail based upon the following drawings. Illustrated are.

DETAILED DESCRIPTION

Figure 1:
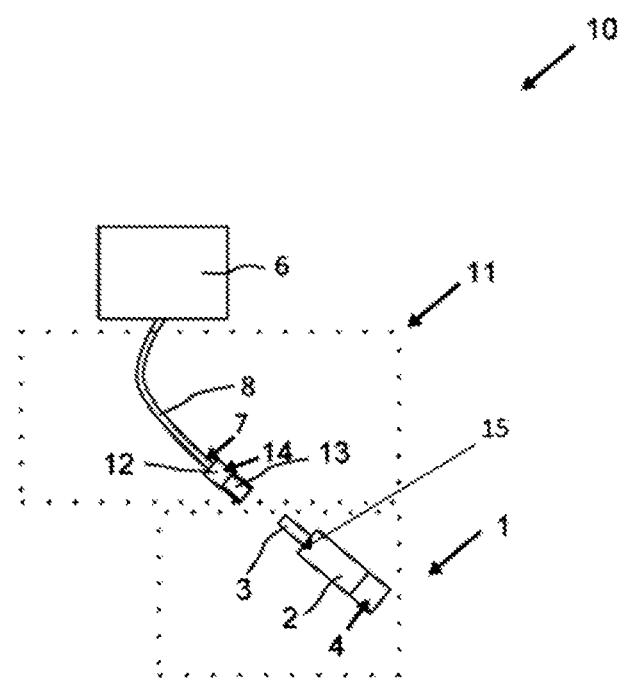
FIG. 1 shows a schematic drawing of a sensor arrangement according to the present disclosure.

FIG. 1 shows a schematic drawing of a sensor arrangement 10. The sensor arrangement 10 comprises a sensor 1 and a connection element 11. A sensor 1 communicates with a superordinate unit 6 via a first interface 3. In this exemplary embodiment, the superordinate unit 6 is designed as a transmitter. The transmitter is in turn connected to a control system (not shown). In this embodiment, the sensor 1 communicates directly with a control system. Connected sensor-side to the transmitter is a cable 8 whose other end comprises a second interface 13 complementary to the first interface 3. The connection element 11 comprises the cable 8, together with the second interface 13. The first and second interfaces 3, 13 are designed as galvanically-separated interface, for example, as inductive interfaces that can be coupled to one another by means of a mechanical plug connection. The mechanical plug connection is hermetically sealed so that no fluid may penetrate from the outside, e.g., the medium to be measured, air, or dust.

Data (bi-directional) and energy (uni-directional, i.e., from transmitter 6 to sensor 1) are sent via the interfaces 3, 13. The sensor arrangement 10 is used predominantly in process automation.

The sensor 1 has a sensor element 4 for detecting a measurement value. The sensor element 4 generates first electrical signals as a function of the measurement value to be measured, which first electrical signals are sent to a data processing unit 14 via the first and second interfaces 3, 13. From the first electrical signals, the data processing unit 14 determines a measurement value (for example, the pH value) and sends second electrical signals dependent upon the measurement value to the superordinate unit 6, so that said superordinate unit 6 may display the measurement value. On the other hand, the data processing unit 14 sends a third electrical signal corresponding to the determined measurement value back to the sensor 1 via the first and second interfaces 3, 13.

The sensor 1 has a light source 15 for transducing the third electrical signal into light of a color corresponding to the measurement value. The light source 15 comprises RGB LED's (red, green, and blue light-emitting diodes) that are combined with one another in an LED housing so that their light mixes well and therefore, with suitable control of the individual light-emitting diodes, appears from the outside to be white. For better light mixing, additional optical components, such as a diffuser, may be provided. With this combination of light-emitting diodes, light of other colors can also be produced via a suitable control of the individual light-emitting diodes; continuous color transitions are also possible.

Figure 2:
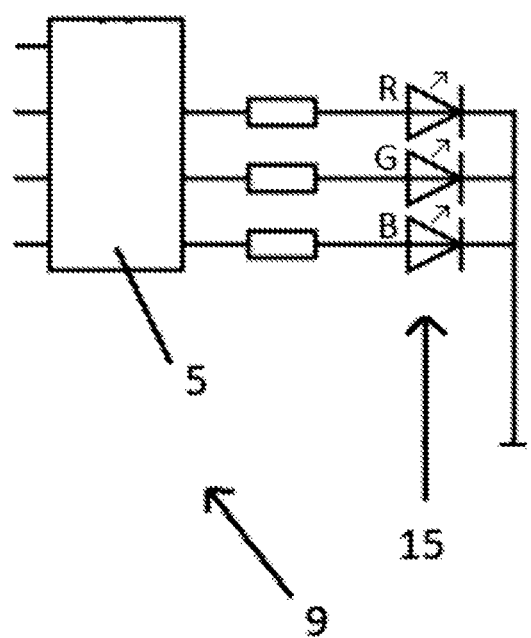
FIG. 2 shows an electronic circuit for showing a color dependent upon the pH value.

FIG. 2 shows an electronic circuit 9 for presentation of the signal dependent upon the measurement value in a color dependent upon the pH value. The circuit 9 comprises a microcontroller 5 for directing the light source 15, which includes a red light-emitting diode, a green light-emitting diode, and a blue light-emitting diode. The microcontroller 5 receives the third electrical signal and, via control of the light source 15, transduces this into a color dependent upon the measurement value, which color is displayed by means of the light source 15.

The electronic circuit 9 may be arranged in the sensor or in a coupling body 2 of the sensor 1 (see FIG. 1). However, the electronic circuit 9 is preferably arranged in the coupling body 2 of the sensor 1 in such a way that the emitted light is radiated out through the vitreous body of the sensor element 4.

Stored in the microcontroller 5 are the color transitions of different pH indicators, which may be selected via an index entry. Depending upon the application, the user may select a pH value with its stored color transitions.

The applications in the non-industrial field are as follows. The first example relates to a swimming pool. The optimal range for the pH value in a pool is between pH 7.0 and 7.4. This is shifted into the alkaline range by the addition of chlorine for disinfection. Since the exact value is thereby of less interest, the measurement is often performed with test strips, which take on a specific coloration depending upon the pH value.

Via the method described above, existing pH sensors may also be modified so that these supply the user with the color interpretation of the measurement value in a familiar form, without a measuring transducer needing to be used.

An additional application is the color monitoring of the measurement value in aquariums. Furthermore, new applications may be developed via the combination of hermetically-sealed pH measurement with a color visualization of the measurement value.

Figure 3:
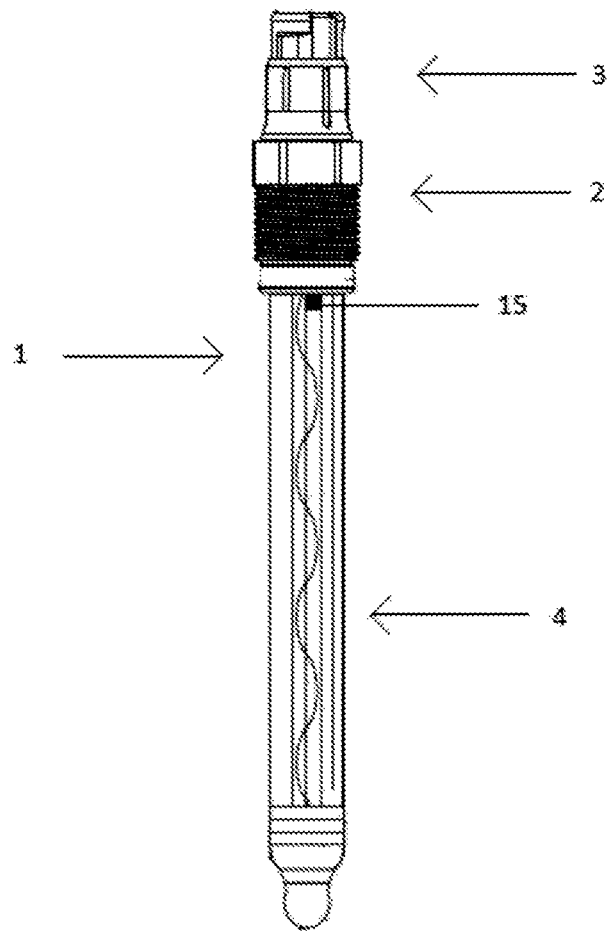
FIG. 3 shows an embodiment of a sensor corresponding to the sensor arrangement FIG. 1.

FIG. 3 shows a drawing of a sensor 1 corresponding to FIG. 1. The sensor 1 has a first coupling body 2 having a first interface 3. A sensor element 4 for detecting a measurement value is arranged on a side of the coupling body 2 situated opposite the first interface 3. A light source 15 for generating light in a color corresponding to the measurement value is likewise located on the side of the coupling body 2 having the sensor element 4.

The invention claimed is:

1. A sensor arrangement for use in process automation, the sensor arrangement comprising:

a sensor including a first coupling body having a sensor element structured to detect a measurement value of the process automation and having a first interface configured to transmit a signal dependent upon the measurement value, the sensor further including a light source; and a connection element structured to transmit the signal to a superordinate unit, the connection element including a second coupling body complementary to the first coupling body and having a second interface complementary to the first interface, wherein the first interface and second interface are configured for bi-directional communication between the sensor and the superordinate unit, wherein the light source is embodied to transduce the signal dependent upon the measurement value into light of a color corresponding to a discrete value of the measurement value, wherein the light source is configured to emit a range of colors of light in which each color corresponds to a different discrete value of the measurement value.

2. The sensor arrangement of claim 1, wherein the light source includes a red light-emitting diode, a green light-emitting diode, and a blue light-emitting diode.

3. The sensor arrangement of claim 1, wherein the light source is disposed in the first coupling body or in the sensor element.

4. The sensor arrangement of claim 1, wherein the sensor element is at least partially composed of glass, and wherein the light source is arranged in the first coupling body such that light emitted from the light source is directed into the glass of the sensor element and is emitted from the sensor element.

5. The sensor arrangement of claim 1, wherein the light source includes a diffuser which is arranged such that light emitted from the light source is radiated diffusely.

6. The sensor arrangement of claim 1, wherein the sensor includes a microcontroller configured to control the light source.

7. The sensor arrangement of claim 6, wherein the discrete values of the measurement values that correspond to color transitions of pH indicators are stored in the microcontroller.

8. The sensor arrangement of claim 7, wherein the corresponding color transitions are selectable by a user.

9. The sensor arrangement of claim 1, wherein the measurement value is a pH value, and wherein the color that corresponds to the discrete value of the measurement value is the color of a pH indicator for the pH value.

10. The sensor arrangement of claim 9, wherein the light source is further configured such that the range of colors of light emitted corresponds to a range of different discrete pH values between 0 and 14.

11. A sensor arrangement for use in process automation, the sensor arrangement comprising:
   a sensor including a first coupling body having a sensor element structured to detect a measurement value of the process automation and having a first interface configured to transmit a signal dependent upon the measurement value;
   a connection element structured to transmit the signal to a superordinate unit, the connection element including a second coupling body complementary to the first coupling body and having a second interface complementary to the first interface, wherein the first interface and second interface are configured for bi-directional communication between the sensor and the superordinate unit; and
   a light source embodied to transduce the signal dependent upon the measurement value into light of a color corresponding to the measurement value,
   wherein the light source is disposed in the first coupling body such that light emitted from the light source is directed into sensor element and is emitted from the sensor element.

* * * * *